United States Patent
Ito

(10) Patent No.: US 9,791,411 B2
(45) Date of Patent: Oct. 17, 2017

(54) PROCESSING APPARATUS INCLUDING A THREE-DIMENSIONAL INTERFEROMETRIC IMAGER

(71) Applicant: DISCO CORPORATION, Tokyo (JP)

(72) Inventor: Yusaku Ito, Tokyo (JP)

(73) Assignee: DISCO CORPORATION, Tokyo (JP)

( * ) Notice: Subject to any disclaimer, the term of this patent is extended or adjusted under 35 U.S.C. 154(b) by 375 days.

(21) Appl. No.: 14/461,912

(22) Filed: Aug. 18, 2014

(65) Prior Publication Data

US 2015/0049171 A1 Feb. 19, 2015

(30) Foreign Application Priority Data

Aug. 19, 2013 (JP) ................. 2013-169748

(51) Int. Cl.
| | |
|---|---|
| *G01B 9/02* | (2006.01) |
| *G01N 27/82* | (2006.01) |
| *H04N 13/02* | (2006.01) |
| *G01B 11/06* | (2006.01) |
| *H01L 21/67* | (2006.01) |
| *H01L 21/68* | (2006.01) |

(52) U.S. Cl.
CPC ......... *G01N 27/82* (2013.01); *G01B 11/0608* (2013.01); *H01L 21/67092* (2013.01); *H01L 21/681* (2013.01); *H04N 13/0203* (2013.01)

(58) Field of Classification Search
CPC . G01N 27/82; H01L 21/681; H01L 21/67092; G01B 11/0608; H04N 13/0203
See application file for complete search history.

(56) References Cited

U.S. PATENT DOCUMENTS

2010/0128276 A1* 5/2010 De Groot ........... G01B 11/2441
356/450

FOREIGN PATENT DOCUMENTS

| JP | 05-326700 | 12/1993 |
|---|---|---|
| JP | 07-045556 | 2/1995 |
| JP | 2002-319559 | 10/2002 |
| JP | 2008-012566 | 1/2008 |

* cited by examiner

*Primary Examiner* — Hwa Lee
(74) *Attorney, Agent, or Firm* — Greer Burns & Crain, Ltd.

(57) ABSTRACT

A processing apparatus including a chuck table for holding a workpiece, a processing unit for processing the workpiece held on the chuck table, and a feeding mechanism for relatively moving the chuck table and the processing unit in an X direction as a feeding direction. The processing apparatus further includes a three-dimensional imaging mechanism for imaging the workpiece held on the chuck table in three dimensions composed of the X direction, a Y direction perpendicular to the X direction, and a Z direction perpendicular to both the X direction and the Y direction and then outputting an image signal obtained above, a control unit for generating a three-dimensional image according to the image signal output from the three-dimensional imaging mechanism, and an output unit for outputting the three-dimensional image generated by the control unit.

6 Claims, 11 Drawing Sheets

PROCESSING APPARATUS INCLUDING A THREE-DIMENSIONAL INTERFEROMETRIC IMAGER

BACKGROUND OF THE INVENTION

Field of the Invention

The present invention relates to a processing apparatus such as a laser processing apparatus, cutting apparatus, and grinding apparatus for performing predetermined processing to a workpiece such as a wafer.

Description of the Related Art

In a semiconductor device fabrication process, a plurality of crossing division lines are formed on the front side of a substantially disk-shaped wafer to thereby define a plurality of separate regions where a plurality of devices such as ICs and LSIs are formed. The back side of the wafer is ground to reduce the thickness of the wafer to a predetermined thickness, and the wafer is next cut along the division lines to thereby divide the regions where the devices are formed from each other, thus obtaining a plurality of individual device chips.

The back side of the wafer is ground by using a grinding apparatus including a chuck table for holding the wafer, grinding means having a grinding wheel for grinding the wafer held on the chuck table, and measuring means for measuring the thickness of the wafer (see Japanese Patent Laid-Open No. 2002-319559, for example).

The wafer is divided along the division lines by using a cutting apparatus or a laser processing apparatus. The cutting apparatus includes a chuck table for holding the wafer, cutting means having a cutting blade for cutting the wafer held on the chuck table, and imaging means for detecting the division lines formed on the wafer held on the chuck table (see Japanese Patent Laid-Open No. Hei 7-45556, for example).

The laser processing apparatus includes a chuck table for holding the wafer, laser beam applying means for applying a laser beam to the wafer held on the chuck table, and imaging means for detecting the division lines formed on the wafer held on the chuck table (see Japanese Patent Laid-Open No. 2008-12566, for example).

In the cutting apparatus or the laser processing apparatus, a cut groove or a laser processed groove is imaged by the imaging means to detect the condition of the cut groove or the condition of the laser processed groove. Accordingly, the processing conditions can be adjusted according to the condition detected above (see Japanese Patent Laid-Open No. Hei 5-326700, for example).

SUMMARY OF THE INVENTION

The image obtained by the imaging means is a two-dimensional image, so that it is impossible to detect the depth or sectional shape of the cut groove, the depth or sectional shape of the laser processed groove, or the condition of debris, for example. Accordingly, the processing conditions cannot be adjusted according to three-dimensional processing.

Further, since the image obtained by the imaging means is a two-dimensional image, the irregular condition of a grinding mark in the grinding apparatus cannot be verified.

It is therefore an object of the present invention to provide a processing apparatus which can verify the processed condition of a workpiece in three dimensions.

In accordance with an aspect of the present invention, there is provided a processing apparatus including workpiece holding means having a holding surface for holding a workpiece; processing means for processing the workpiece held on the holding surface of the workpiece holding means; feeding means for relatively moving the workpiece holding means and the processing means in an X direction as a feeding direction; a three-dimensional imaging mechanism for imaging the workpiece held on the holding surface of the workpiece holding means in three dimensions composed of the X direction, a Y direction perpendicular to the X direction, and a Z direction perpendicular to both the X direction and the Y direction and then outputting an image signal obtained above; control means for generating a three-dimensional image according to the image signal output from the three-dimensional imaging mechanism; and output means for outputting the three-dimensional image generated by the control means.

Preferably, the three-dimensional imaging mechanism includes an imaging device having a plurality of pixels arranged in the X direction and the Y direction, focusing means opposed to the holding surface of the workpiece holding means, light applying means for applying light through the focusing means to the workpiece held on the holding surface of the workpiece holding means, interference light generating means for generating interference light according to return light reflected on the workpiece held on holding surface of the workpiece holding means, Z direction moving means for moving the focusing means in the Z direction, and Z position detecting means for detecting the Z position of the focusing means to be moved by the Z direction moving means; and the control means obtains the X and Y coordinates of the pixels in the imaging device means that have captured the interference light having a high intensity as generated by the interference light generating means at every Z position according to a Z position signal from the Z position detecting means and an image signal from the imaging device means and then generates the three-dimensional image according to the X and Y coordinates obtained at every Z position.

Preferably, the focusing means includes a unit case and an objective lens provided in the unit case; the interference light generating means includes a glass plate provided in the unit case so as to be interposed between the objective lens and the holding surface of the workpiece holding means, the glass plate having a central microscopic mirror to generate the interference light, and a first beam splitter provided in the unit case so as to be interposed between the glass plate and the holding surface of the workpiece holding means for partially transmitting the light applied from the light applying means and applying the transmitted light to the workpiece held on the holding surface of the workpiece holding means and for also partially reflecting the light applied from the light applying means and directing the reflected light toward the microscopic mirror of the glass plate; and the light applying means includes a light source for emitting light and a second beam splitter provided between the imaging device and the focusing means for guiding the light emitted from the light source toward the focusing means and also guiding the light reflected from the workpiece held on the holding surface of the workpiece holding means toward the imaging device means.

Preferably, the Z direction moving means includes first Z direction moving means for moving the three-dimensional imaging mechanism in the Z direction and second Z direction moving means for moving the focusing means in the Z direction. More preferably, the second Z direction moving means includes a piezoelectric motor.

As described above, the processing apparatus according to the present invention includes the three-dimensional imaging mechanism for imaging the workpiece held by the workpiece holding means in three dimensions composed of the X direction, the Y direction, and the Z direction perpendicular to each other and then outputting an image signal obtained above, the control means for generating a three-dimensional image according to the image signal output from the three-dimensional imaging mechanism, and the output means such as display means for displaying the three-dimensional image generated by the control means. Accordingly, the processed condition of a processed portion of the workpiece processed by the processing means can be verified according to the three-dimensional image displayed by the display means as an example of the output means, so that the current processing conditions can be adjusted to set proper processing conditions.

The above and other objects, features and advantages of the present invention and the manner of realizing them will become more apparent, and the invention itself will best be understood from a study of the following description and appended claims with reference to the attached drawings showing a preferred embodiment of the invention.

DETAILED DESCRIPTION OF THE PREFERRED EMBODIMENT

Figure 1:
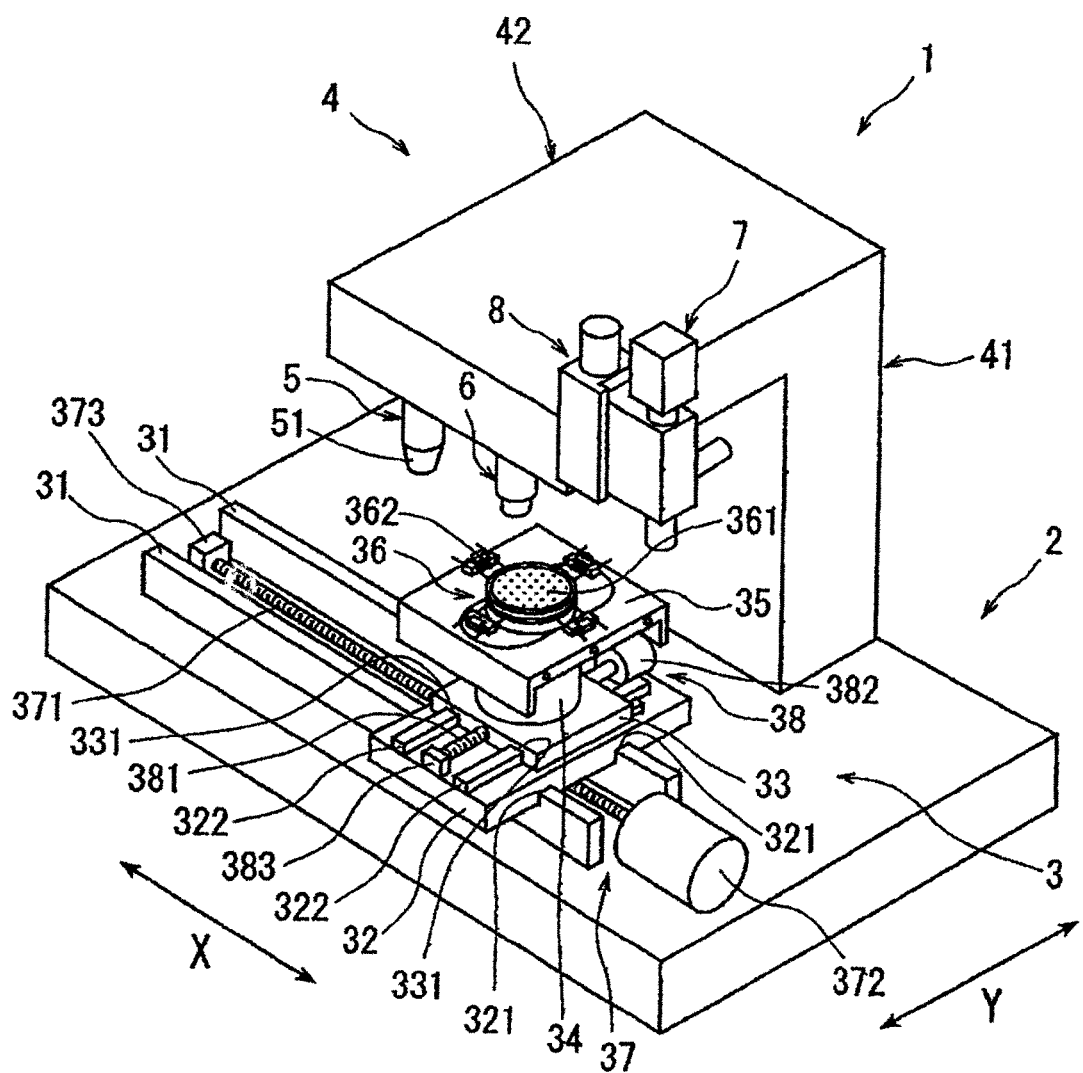
FIG. 1 is a perspective view of a laser processing apparatus as the processing apparatus according to the present invention.

A preferred embodiment of the processing apparatus according to the present invention will now be described in detail with reference to the attached drawings. FIG. 1 is a perspective view of a laser processing apparatus 1 as the processing apparatus according to the present invention. The laser processing apparatus 1 shown in FIG. 1 includes a stationary base 2, a chuck table mechanism 3 for holding a workpiece, the chuck table mechanism 3 being provided on the stationary base 2 so as to be movable in a feeding direction (X direction) shown by an arrow X, and a laser beam applying unit 4 provided on the stationary base 2, the laser beam applying unit 4 having laser beam applying means as processing means.

The chuck table mechanism 3 includes a pair of guide rails 31 provided on the stationary base 2 so as to extend parallel to each other in the X direction, a first slide block 32 provided on the guide rails 31 so as to be movable in the X direction, a second slide block 33 provided on the first slide block 32 so as to be movable in an indexing direction (Y direction) shown by an arrow Y perpendicular to the X direction, a cover table 35 supported by a cylindrical member 34 standing on the second slide block 33, and a chuck table 36 as workpiece holding means. The chuck table 36 has a vacuum chuck 361 formed of a porous material. A workpiece such as a disk-shaped semiconductor wafer is adapted to be held under suction on the upper surface of the vacuum chuck 361 as a holding surface by operating suction means (not shown). The chuck table 36 is rotatable by a pulse motor (not shown) provided in the cylindrical member 34. The chuck table 36 is provided with clamps 362 for fixing an annular frame supporting a semiconductor wafer as the workpiece through a protective tape.

The lower surface of the first slide block 32 is formed with a pair of guided grooves 321 for slidably engaging the pair of guide rails 31 mentioned above. A pair of guide rails 322 are provided on the upper surface of the first slide block 32 so as to extend parallel to each other in the Y direction. Accordingly, the first slide block 32 is movable in the X direction along the guide rails 31 by the slidable engagement of the guided grooves 321 with the guide rails 31. The chuck table mechanism 3 further includes feeding means 37 for moving the first slide block 32 in the X direction along the guide rails 31. The feeding means 37 includes an externally threaded rod 371 extending parallel to the guide rails 31 so as to be interposed therebetween and a pulse motor 372 as a drive source for rotationally driving the externally threaded rod 371. The externally threaded rod 371 is rotatably supported at one end thereof to a bearing block 373 fixed to the stationary base 2 and is connected at the other end to the output shaft of the pulse motor 372 so as to receive the torque thereof. The externally threaded rod 371 is engaged with a tapped through hole formed in an internally threaded block (not shown) projecting from the lower surface of the first slide block 32 at a central portion thereof. Accordingly, the first slide block 32 is moved in the X direction along the guide rails 31 by operating the pulse motor 372 to normally or reversely rotate the externally threaded rod 371.

The lower surface of the second slide block 33 is formed with a pair of guided grooves 331 for slidably engaging the pair of guide rails 322 provided on the upper surface of the first slide block 32 as mentioned above. Accordingly, the second slide block 33 is movable in the Y direction along the guide rails 322 by the slidable engagement of the guided grooves 331 with the guide rails 322. The chuck table mechanism 3 further includes indexing means 38 for moving the second slide block 33 in the Y direction along the guide rails 322. The indexing means 38 includes an externally threaded rod 381 extending parallel to the guide rails 322 so as to be interposed therebetween and a pulse motor 382 as a drive source for rotationally driving the externally threaded rod 381. The externally threaded rod 381 is rotatably supported at one end thereof to a bearing block 383 fixed to the upper surface of the first slide block 32 and is connected at the other end to the output shaft of the pulse motor 382 so as to receive the torque thereof. The externally threaded rod 381 is engaged with a tapped through hole formed in an internally threaded block (not shown) projecting from the lower surface of the second slide block 33 at a central portion thereof. Accordingly, the second slide block 33 is moved in the Y direction along the guide rails 322 by operating the pulse motor 382 to normally or reversely rotate the externally threaded rod 381.

The laser beam applying unit 4 includes a support member 41 provided on the stationary base 2, a unit casing 42 supported by the support member 41 so as to extend in a substantially horizontal direction, laser beam applying means 5 provided on the unit casing 42, and imaging means 6 for detecting a subject area to be laser-processed. The laser beam applying means 5 includes pulsed laser beam oscillating means (not shown) provided in the unit casing 42 and a processing head 51 for focusing a pulsed laser beam oscillated by the pulsed laser beam oscillating means and applying this pulsed laser beam to the workpiece held on the chuck table 36. The pulsed laser beam oscillating means includes a pulsed laser oscillator and repetition frequency setting means.

The imaging means 6 is provided on the unit casing 42 at a position lying on an extension line extending from the processing head 51 in the X direction so as to be spaced a predetermined distance. The imaging means 6 includes an ordinary imaging device (CCD) for imaging the workpiece by using visible light, infrared light applying means for applying infrared light to the workpiece, an optical system for capturing the infrared light applied to the workpiece by the infrared light applying means, and an imaging device (infrared CCD) for outputting an electrical signal corresponding to the infrared light captured by the optical system. An image signal output from the imaging means 6 is transmitted to first control means (not shown).

The laser processing apparatus 1 further includes a three-dimensional imaging mechanism 7 provided on the unit casing 42 for imaging the workpiece held on the chuck table 36 in three dimensions composed of the X direction, the Y direction perpendicular to the X direction, and the Z direction perpendicular to both the X direction and the Y direction and then outputting an image signal obtained above. The three-dimensional imaging mechanism 7 is supported to first Z direction moving means 8 provided on the unit casing 42 so as to be movable in the Z direction by the first Z direction moving means 8. The three-dimensional imaging mechanism 7 and the first Z direction moving means 8 will now be described in detail with reference to FIGS. 2 to 4.

Figure 2:
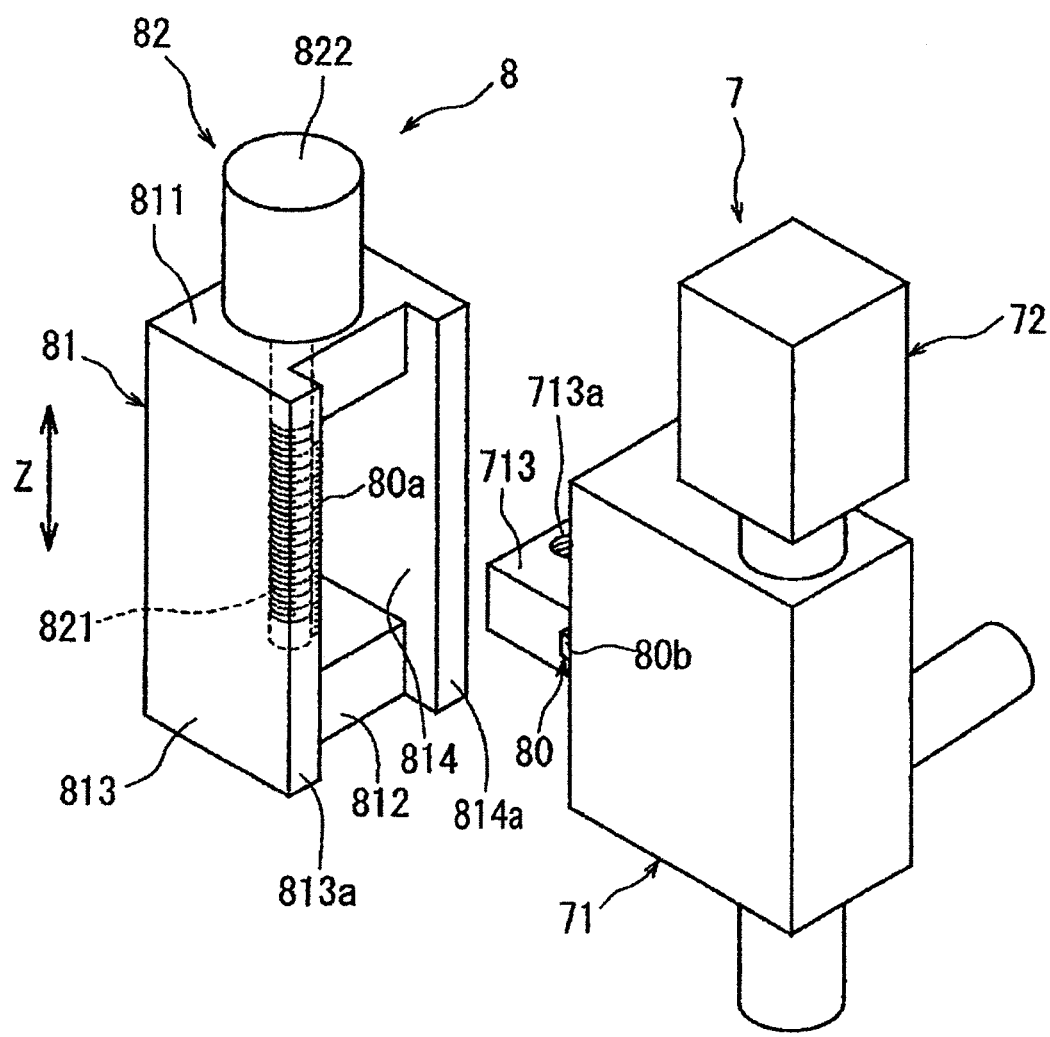
FIG. 2 is an exploded perspective view of a three-dimensional imaging mechanism and first Z direction moving means included in the laser processing apparatus shown in FIG. 1.
Figure 3:
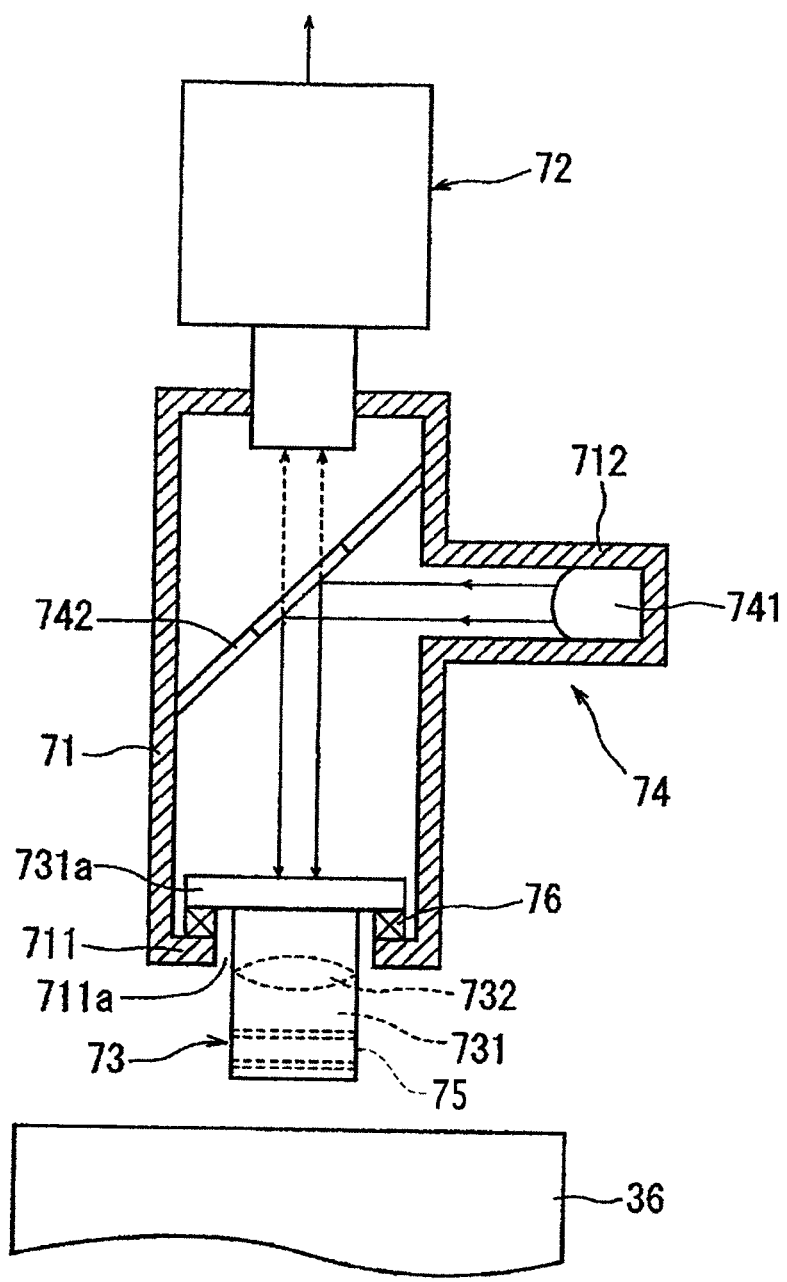
FIG. 3 is a sectional view showing an essential part of the three-dimensional imaging mechanism shown in FIG. 2.
Figure 4:
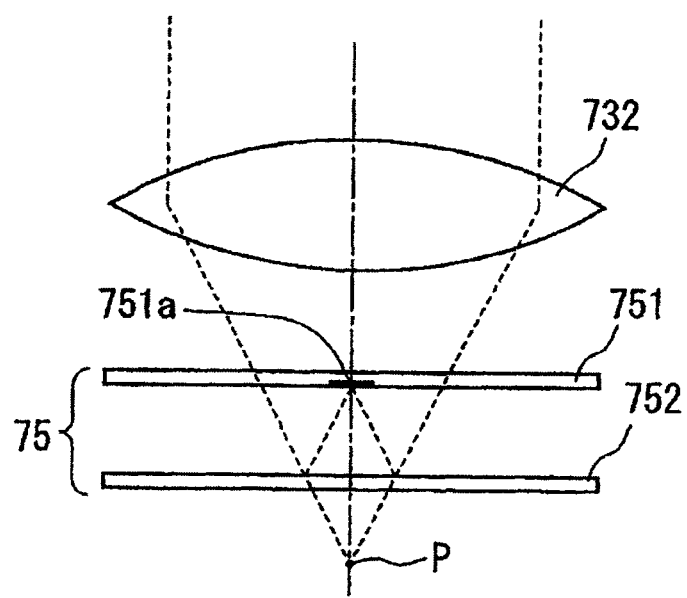
FIG. 4 is a schematic view for illustrating focusing means and interference light generating means included in the three-dimensional imaging mechanism shown in FIG. 3.

The three-dimensional imaging mechanism 7 shown in FIGS. 2 to 4 is a so-called Mirau type three-dimensional imaging mechanism. As shown in FIG. 3 in detail, the three-dimensional imaging mechanism 7 includes a mechanism housing 71, imaging device means 72 provided at the upper portion of the mechanism housing 71, focusing means 73 provided at the lower portion of the mechanism housing 71 so as to be opposed to the holding surface (upper surface) of the chuck table 36, and light applying means 74 for applying light through the focusing means 73 to the workpiece held on the holding surface of the chuck table 36. The imaging device means 72 includes a plurality of pixels arranged in the X direction and the Y direction and outputs an image signal to second control means which will be hereinafter described.

The focusing means 73 constituting the three-dimensional imaging mechanism 7 is composed of a unit case 731 and an objective lens 732 provided in the unit case 731. As shown in FIG. 4, the objective lens 732 functions to focus the light from the light applying means 74 to a focal point P. In this preferred embodiment, the focused spot diameter at the focal point P is set to 100 μm. Further, interference light generating means 75 is provided in the unit case 731 of the focusing means 73. The interference light generating means 75 functions to generate interference light according to return light reflected on the workpiece held on the holding surface of the chuck table 36. As shown in FIG. 4, the interference light generating means 75 is composed of a glass plate 751 interposed between the objective lens 732 and the chuck table 36 and a first beam splitter 752 interposed between the glass plate 751 and the chuck table 36. The glass plate 751 is provided with a central microscopic mirror 751a having a diameter of 0.5 mm, for example. The first beam splitter 752 functions to partially transmit the light applied from the light applying means 74 and focused by the objective lens 732, thereby applying the transmitted light to the workpiece held on the holding surface of the chuck table 36 and also to partially reflect the light applied from the light applying means 74 and focused by the objective lens 732, thereby directing the reflected light toward the mirror 751a of the glass plate 751. The transmitted light through the first beam splitter 752 is reflected at the focal point P to interfere with the reflected light from the first beam splitter 752 on the glass plate 751. Thus, the focusing means 73 and the interference light generating means 75 cooperate to generate interference light having a high intensity and guide this interference light toward the imaging device means 72.

As shown in FIG. 3, the mechanism housing 71 has a bottom wall 711 formed with a mount hole 711a. The unit case 731 containing the objective lens 732 and the interference light generating means 75 is mounted to the mechanism housing 71 so as to be movable through the mount hole 711a of the bottom wall 711 in a direction (vertical direction as viewed in FIG. 3) perpendicular to the holding surface (upper surface) of the chuck table 36. A flange portion 731a is provided at the upper end of the unit case 731, and an actuator 76 is provided between the bottom wall 711 of the mechanism housing 71 and the flange portion 731a of the unit case 731 of the focusing means 73. The actuator 76 functions as second Z direction moving means for moving the unit case 731 in the vertical direction as viewed in FIG. 3. In this preferred embodiment, the actuator 76 is provided by a piezoelectric motor including a piezoelectric element adapted to axially extend according to a voltage applied. Accordingly, the actuator 76 provided by such a piezoelectric motor can move the unit case 731 in the vertical direction as viewed in FIG. 3 (in the direction perpendicular to the holding surface of the chuck table 36) according to a voltage applied under the control by the second control means to be hereinafter described. As a modification, a high-responsive voice coil motor may be used for the actuator 76.

The light applying means 74 is composed of a light source 741 such as an LED provided in a side projection 712 projecting from one side surface of the mechanism housing 71 and a second beam splitter 742 provided in the mechanism housing 71 at a position between the imaging device means 72 and the focusing means 73. The second beam splitter 742 functions to guide the light emitted from the light source 741 toward the focusing means 73 and also to guide the light reflected from the workpiece held on the holding surface of the chuck table 36 toward the imaging device means 72.

The configuration of the first Z direction moving means 8 will now be described in detail with reference to FIG. 2. The first Z direction moving means 8 is composed of a support case 81 for supporting the mechanism housing 71 of the three-dimensional imaging mechanism 7 so that the mechanism housing 71 is movable in the Z direction shown by an arrow Z (in the direction perpendicular to the holding surface of the chuck table 36) and operating means 82 for moving the mechanism housing 71 supported to the support case 81 in the Z direction. The support case 81 is composed of an upper wall 811, a bottom wall 812, opposite side walls 813 and 814, and a rear wall (not shown). The opposite side walls 813 and 814 project to the front side to form a pair of guide rails 813a and 814a. The operating means 82 includes an externally threaded rod 821 extending parallel to the opposite side walls 813 and 814 of the support case 81 so as to be interposed therebetween. The externally threaded rod 821 is rotatably supported to the upper wall 811 and the bottom wall 812. The operating means 82 further includes a pulse motor 822 as a drive source provided on the upper wall 811 for rotationally driving the externally threaded rod 821. An internally threaded block 713 having a tapped through hole 713a is provided on the rear wall of the mechanism housing 71. The tapped through hole 713a of the internally threaded block 713 is threadedly engaged with the externally threaded rod 821 of the operating means 82. Accordingly, the mechanism housing 71 having the internally threaded block 713 is moved along the guide rails 813a and 814a in the Z direction by operating the pulse motor 822 to normally or reversely rotate the externally threaded rod 821.

The laser processing apparatus 1 further includes Z position detecting means 80 for detecting the Z position of the three-dimensional imaging mechanism 7 to be moved by the first Z direction moving means 8. The Z position detecting means 80 is composed of a linear scale 80a provided on the guide rail 813a and a read head 80b mounted on the mechanism housing 71 of the three-dimensional imaging mechanism 7 and movable along the linear scale 80a together with the mechanism housing 71. The read head 80b of the Z position detecting means 80 transmits a pulse signal of one pulse every 1 μm in this embodiment, for example, to the second control means which will be hereinafter described.

Figure 5:
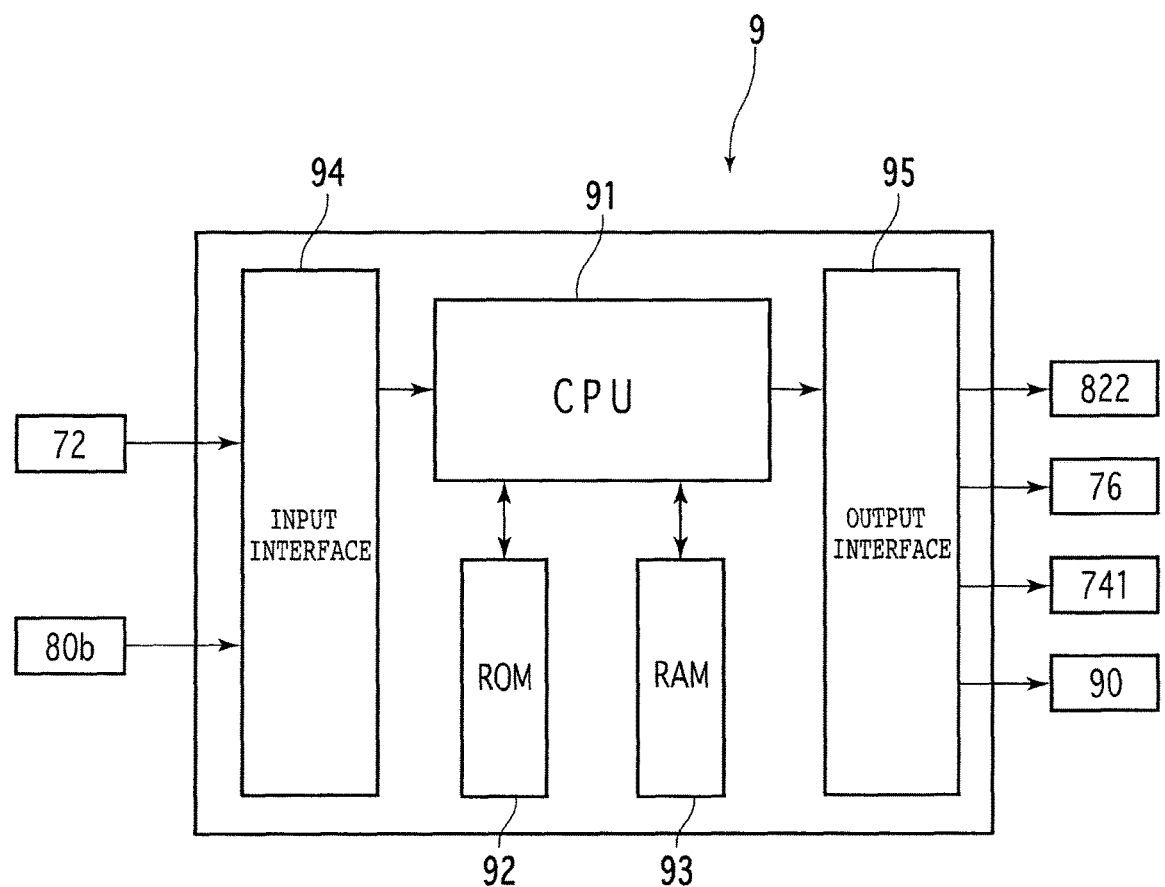
FIG. 5 is a block diagram of second control means included in the laser processing apparatus shown in FIG. 1.

The laser processing apparatus 1 further includes second control means 9 shown in FIG. 5. The second control means 9 functions to generate a three-dimensional image according to a detection signal output from the imaging device means 72 of the three-dimensional imaging mechanism 7. The second control means 9 is configured by a computer, and it includes a central processing unit (CPU) 91 for performing operational processing according to a control program, a read only memory (ROM) 92 for preliminarily storing the control program, a random access memory (RAM) 93 for storing the results of computation, etc., an input interface 94, and an output interface 95. Detection signals from the imaging device means 72 of the three-dimensional imaging mechanism 7 and the read head 80b of the Z position detecting means 80 for detecting the Z position of the three-dimensional imaging mechanism 7 are input into the input interface 94 of the second control means 9. On the other hand, control signals are output from the output interface 95 of the second control means 9 to the pulse motor 822 of the first Z direction moving means 8, the actuator 76 provided by a piezoelectric motor functioning as the second Z direction moving means, the light source 741 of the light applying means 74, and output means 90 such as display means and a printer. The random access memory (RAM) 93 preliminarily stores a control map shown in FIG. 6 for setting the relation between a voltage applied to the actuator 76 provided by a piezoelectric motor and an axial displacement of the piezoelectric motor.

Figure 7:
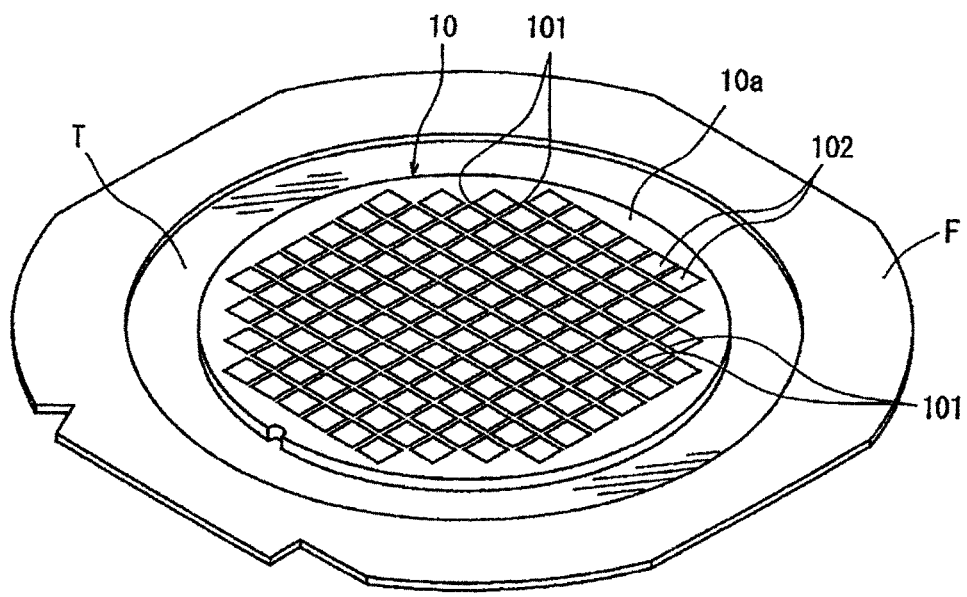
FIG. 7 is a perspective view of a semiconductor wafer as a workpiece in the condition where the semiconductor wafer is attached to a dicing tape supported to an annular frame.

The operation of the laser processing apparatus 1 configured above will now be described. FIG. 7 is a perspective view of a semiconductor wafer 10 as a workpiece to be processed by the laser processing apparatus 1 in the condition where the semiconductor wafer 10 is attached to a dicing tape T supported to an annular frame F. The semiconductor wafer 10 shown in FIG. 7 is a silicon wafer. A plurality of crossing division lines 101 are formed on the front side 10a of the semiconductor wafer 10 to define a plurality of separate regions where a plurality of devices 102 such as ICs and LSIs are respectively formed.

Laser processing using the laser processing apparatus 1 is performed in such a manner that a laser beam is applied to the semiconductor wafer 10 along the division lines 101 to thereby form a laser processed groove along each division line 101 on the front side 10a of the semiconductor wafer 10. First, the semiconductor wafer 10 supported through the dicing tape T to the annular frame F is placed on the chuck table 36 of the laser processing apparatus 1 shown in FIG. 1 in the condition where the dicing tape T is in contact with the upper surface of the chuck table 36. Thereafter, the suction means (not shown) is operated to hold the semiconductor wafer 10 through the dicing tape T on the chuck table 36 under suction. Accordingly, the semiconductor wafer 10 is held through the dicing tape T on the chuck table 36 in the condition where the front side 10a of the semiconductor wafer 10 is oriented upward. Further, the annular frame F supporting the dicing tape T is fixed by the clamps 362 provided on the chuck table 36. Thereafter, the feeding means 37 is operated to move the chuck table 36 holding the semiconductor wafer 10 under suction to a position directly below the imaging means 6.

In the condition where the chuck table 36 is positioned directly below the imaging means 6, an alignment operation is performed by the imaging means 6 and the first control means (not shown) to detect a subject area of the semiconductor wafer 10 to be laser-processed. More specifically, the imaging means 6 and the first control means (not shown) perform image processing such as pattern matching for making the alignment of the division lines 101 extending in a first direction on the semiconductor wafer 10 and the processing head 51 of the laser beam applying means 5, thus performing the alignment for the division lines 101 extending in the first direction. Similarly, this alignment is performed for the other division lines 101 extending in a second direction perpendicular to the first direction on the semiconductor wafer 10.

Figure 8A:
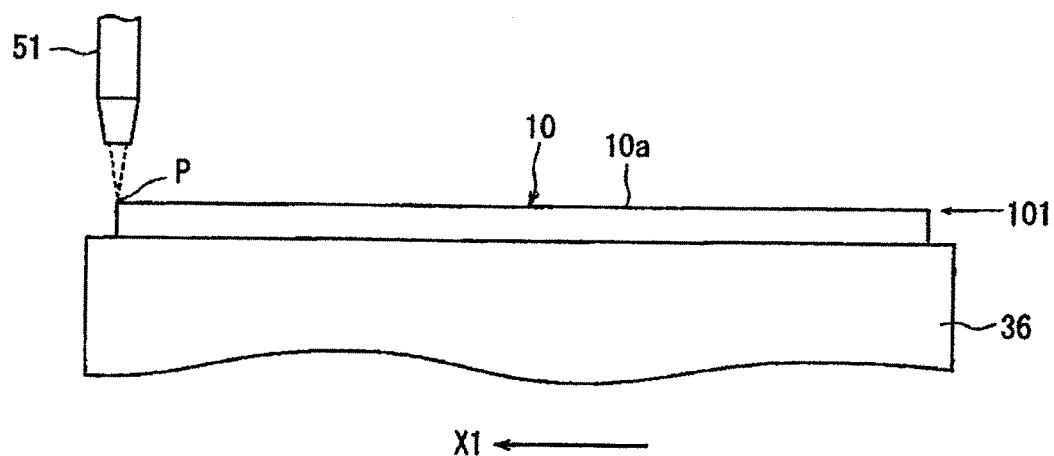
FIGS. 8A to 8C are views for illustrating a laser processed groove forming step by the laser processing apparatus shown in FIG. 1.
Figure 8B:
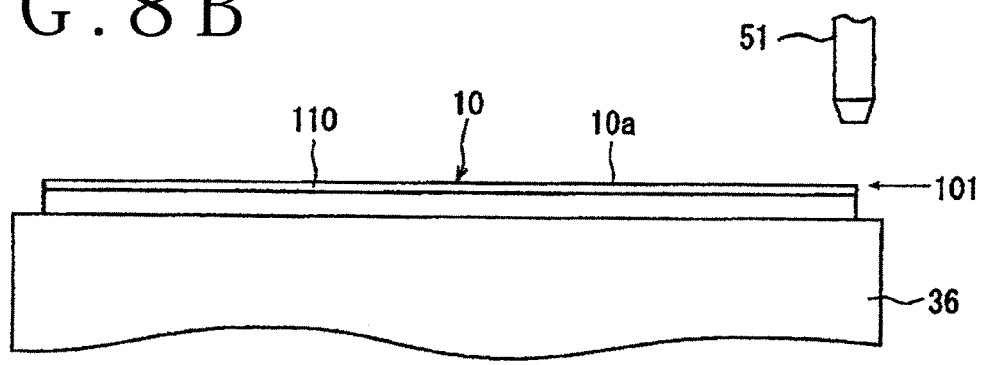
Figure 8C:
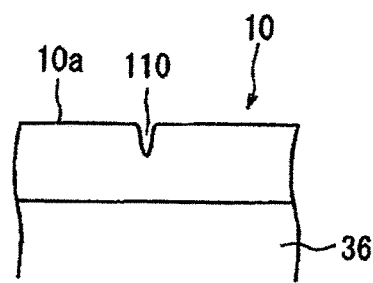

After performing the alignment operation mentioned above, the chuck table 36 is moved to position one end (left end as viewed in FIG. 8A) of a predetermined one of the division lines 101 extending in the first direction directly below the processing head 51 of the laser beam applying means 5 as shown in FIG. 8A. Further, the focal point P of the pulsed laser beam to be applied from the processing head 51 is set near the front side 10a (upper surface) of the semiconductor wafer 10. Thereafter, a pulsed laser beam having an absorption wavelength to the semiconductor wafer 10 is applied from the processing head 51 of the laser beam applying means 5 to the semiconductor wafer 10, and the chuck table 36 is moved at a predetermined feed speed in the direction shown by an arrow X1 in FIG. 8A. When the other end (right end as viewed in FIG. 8B) of the predetermined division line 101 reaches the position directly below the processing head 51 as shown in FIG. 8B, the application of the pulsed laser beam is stopped and the movement of the chuck table 36 is also stopped. As a result, a laser processed groove 110 is formed along the predetermined division line 101 on the front side 10a of the semiconductor wafer 10 as shown in FIGS. 8B and 8C (laser processed groove forming step).

For example, the laser processed groove forming step mentioned above is performed under the following processing conditions.

Figure 6:
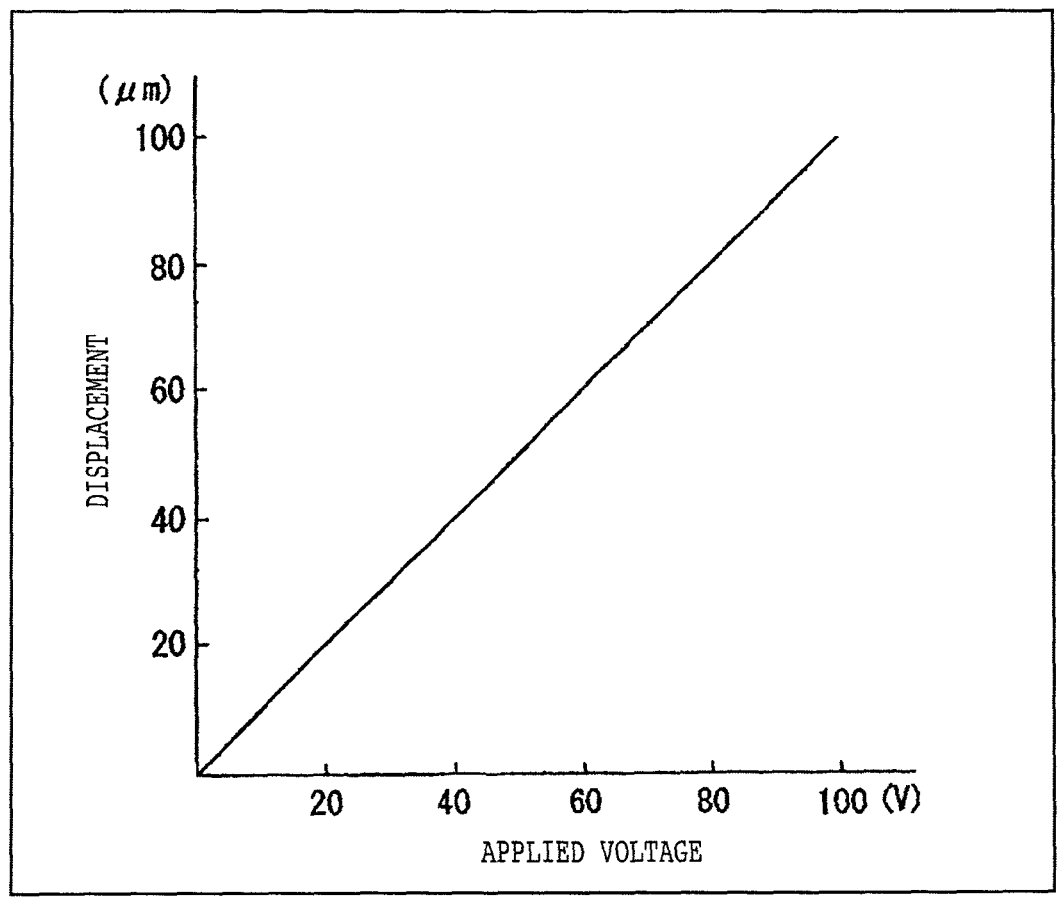
FIG. 6 is a control map setting the relation between a voltage applied to an actuator provided by a piezoelectric motor and an axial displacement of the piezoelectric motor.

Wavelength: 355 nm
Repetition frequency: 50 kHz
Average power: 5 W
Focused spot diameter: 10 μm
Work feed speed: 200 mm/s Thereafter, a laser processed groove checking step is performed to check the processed condition of the laser processed groove 110 formed by performing the laser processed groove forming step mentioned above. First, the feeding means 37 is operated to move the chuck table 36 holding the semiconductor wafer 10 processed by the laser processed groove forming step to a position directly below the focusing means 73 of the three-dimensional imaging mechanism 7 so that the laser processed groove 110 formed on the semiconductor wafer 10 is positioned directly below the focusing means 73. Thereafter, the first Z direction moving means 8 is operated to lower the three-dimensional imaging mechanism 7 from a predetermined standby position. Further, a voltage of 60 V, for example, is applied to the actuator 76 provided by a piezoelectric motor as the second Z direction moving means to thereby axially extend the actuator 76 by an amount of 60 μm as shown in FIG. 6. In this extended condition, the focal point P (see FIG. 4) of light to be applied from the focusing means 73 of the three-dimensional imaging mechanism 7 is set near the front side 10a (upper surface) of the semiconductor wafer 10 held on the chuck table 36.

Figure 9A:
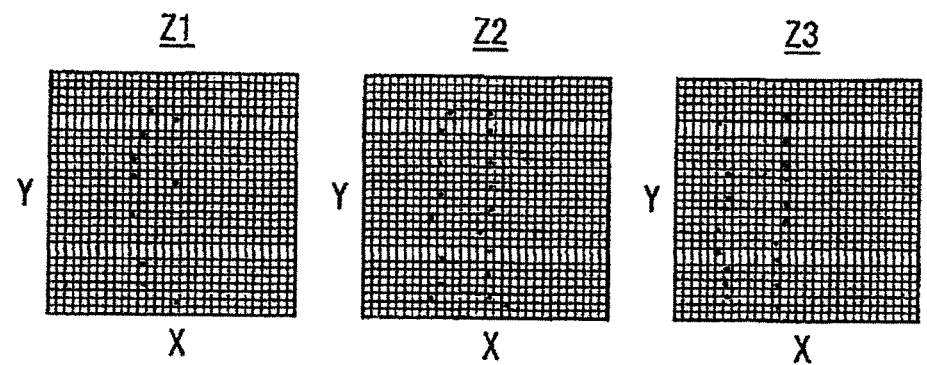
FIGS. 9A and 9B are views for illustrating a laser processed groove checking step by the laser processing apparatus shown in FIG. 1.

Thereafter, the imaging device means 72 and the light source 741 of the light applying means 74 constituting the three-dimensional imaging mechanism 7 are operated and the voltage applied to the actuator 76 as a piezoelectric motor is reduced from 60 V in steps of 1 V. As a result, the actuator 76 as a piezoelectric motor is reduced in length in steps of 1 μm every 1 V as apparent from FIG. 6, so that the focusing means 73 is lowered in the Z direction in steps of 1 μm. Every time the focusing means 73 is lowered in steps of 1 μm, the imaging device means 72 forms an image and transmits an image signal to the second control means 9. According to the image signal transmitted from the imaging device means 72, the second control means 9 obtains the X and Y coordinates of the pixels detecting the interference light having a high intensity at a plurality of Z positions (Z1, Z2, Z3, . . . ) as shown in FIG. 9A and then stores the X and Y coordinates obtained above into the random access memory (RAM) 93. The Z positions (Z1, Z2, Z3, . . . ) can be obtained from a detection signal from the read head 80b of the Z position detecting means 80 or a voltage signal applied to the actuator 76 as a piezoelectric motor.

Figure 9B:
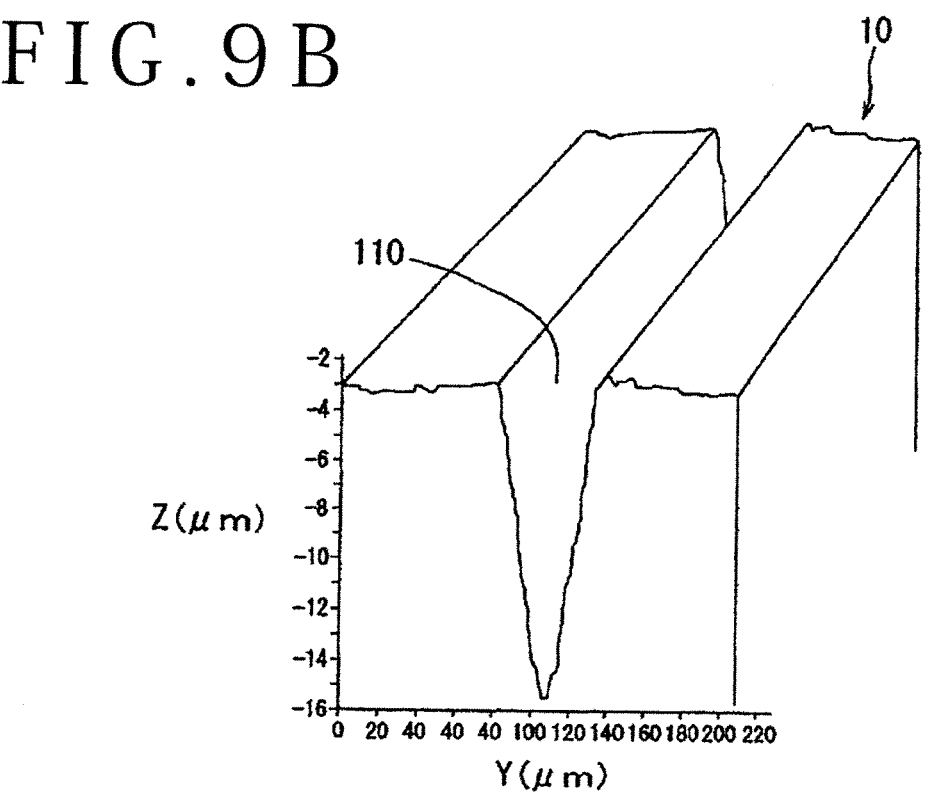

Since the piezoelectric motor can be operated at high speeds, image information can be obtained in a short time. Accordingly, not only the Z position detecting means 80, but also the second control means 9 itself for controlling the voltage to be applied to the actuator 76 as a piezoelectric motor functions as Z position detecting means for detecting the Z position of the focusing means 73. Thereafter, according to the X and Y coordinates of the pixels detecting the interference light having a high intensity at the plural Z positions (Z1, Z2, Z3, . . . ) as stored in the random access memory (RAM) 93, the second control means 9 creates a three-dimensional image of the laser processed groove 110 formed on the semiconductor wafer 10 as shown in FIG. 9B. Thereafter, the second control means 9 outputs the three-dimensional image to the output means 90 to thereby display it on display means such as a monitor or print it out through a printer. In this manner, the three-dimensional image of the laser processed groove 110 is displayed by display means such as a monitor as the output means 90 or printed out by a printer as the output means 90. Accordingly, the operator can verify the processed condition of the laser processed groove 110, so that the current processing conditions can be adjusted to set proper processing conditions.

In this preferred embodiment, the laser processed groove checking step is performed in the condition where the semiconductor wafer 10 processed by the laser processed groove forming step is held on the chuck table 36. As a modification, a table dedicated to the laser processed groove checking step may be provided and the semiconductor wafer 10 processed by the laser processed groove forming step may be held on this table to perform the laser processed groove checking step.

Figure 10:
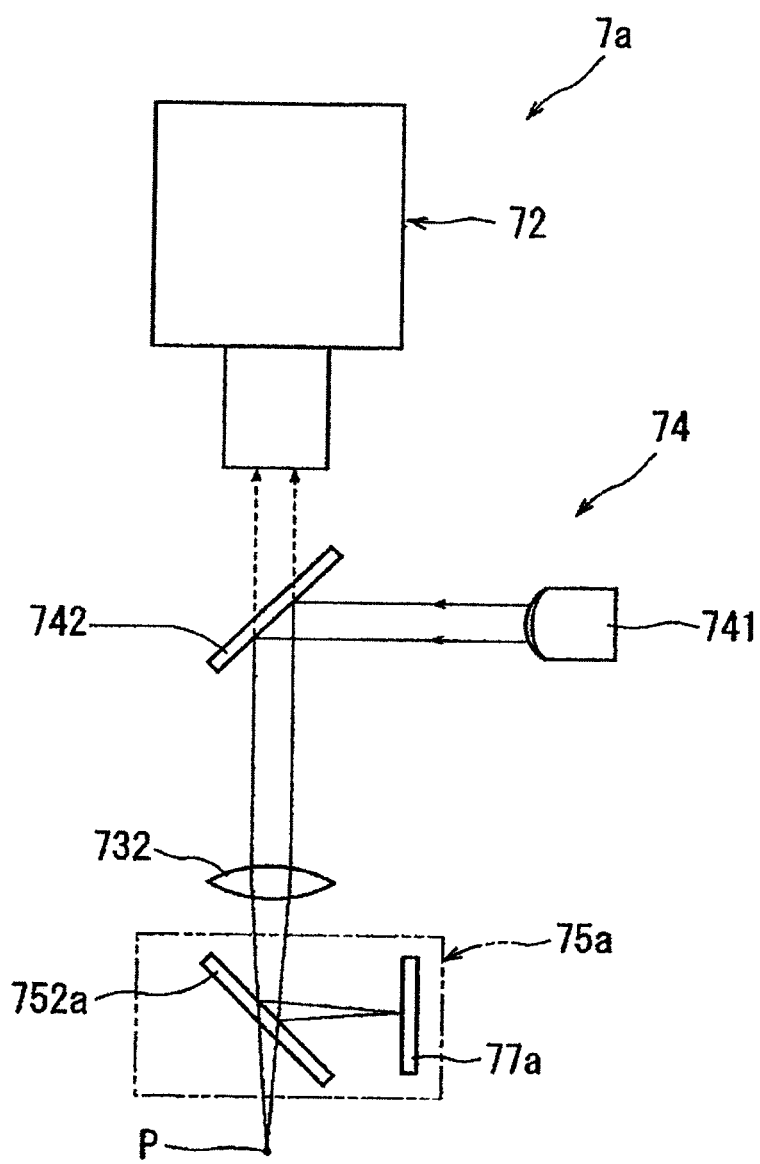
FIG. 10 is a schematic view showing another preferred embodiment of the three-dimensional imaging mechanism.

Another preferred embodiment of the three-dimensional imaging mechanism in the present invention will now be described with reference to FIG. 10. FIG. 10 shows a three-dimensional imaging mechanism 7a, which is a so-called Michelson type three-dimensional imaging mechanism. The three-dimensional imaging mechanism 7a shown in FIG. 10 is different in the configuration of the interference light generating means from the three-dimensional imaging mechanism 7 shown in FIGS. 3 and 4. However, the other components are substantially similar to those shown in FIGS. 3 and 4, so that substantially the same parts are denoted by the same reference symbols and the description thereof will be omitted herein.

As shown in FIG. 10, the three-dimensional imaging mechanism 7a includes interference light generating means 75a composed of a first beam splitter 752a and a reflection mirror 77a. The first beam splitter 752a is interposed between the objective lens 732 and the chuck table 36. The reflection mirror 77a is located at a focal position of light focused by the objective lens 732 and reflected by the first beam splitter 752a. The light emitted from the light source 741 of the light applying means 74 is reflected by the second beam splitter 742 and next focused by the objective lens 732. The light focused by the objective lens 732 is partially transmitted through the first beam splitter 752a and next reflected at the focal point P on the workpiece. On the other hand, the light focused by the objective lens 732 is partially reflected by the first beam splitter 752a to reach the reflection mirror 77a and next reflected on the reflection mirror 77a. The return light from the focal point P interferes with the reflected light from the reflection mirror 77a on the first beam splitter 752a. As a result, interference light having a high intensity is generated and guided toward the imaging device means 72.

Figure 11:
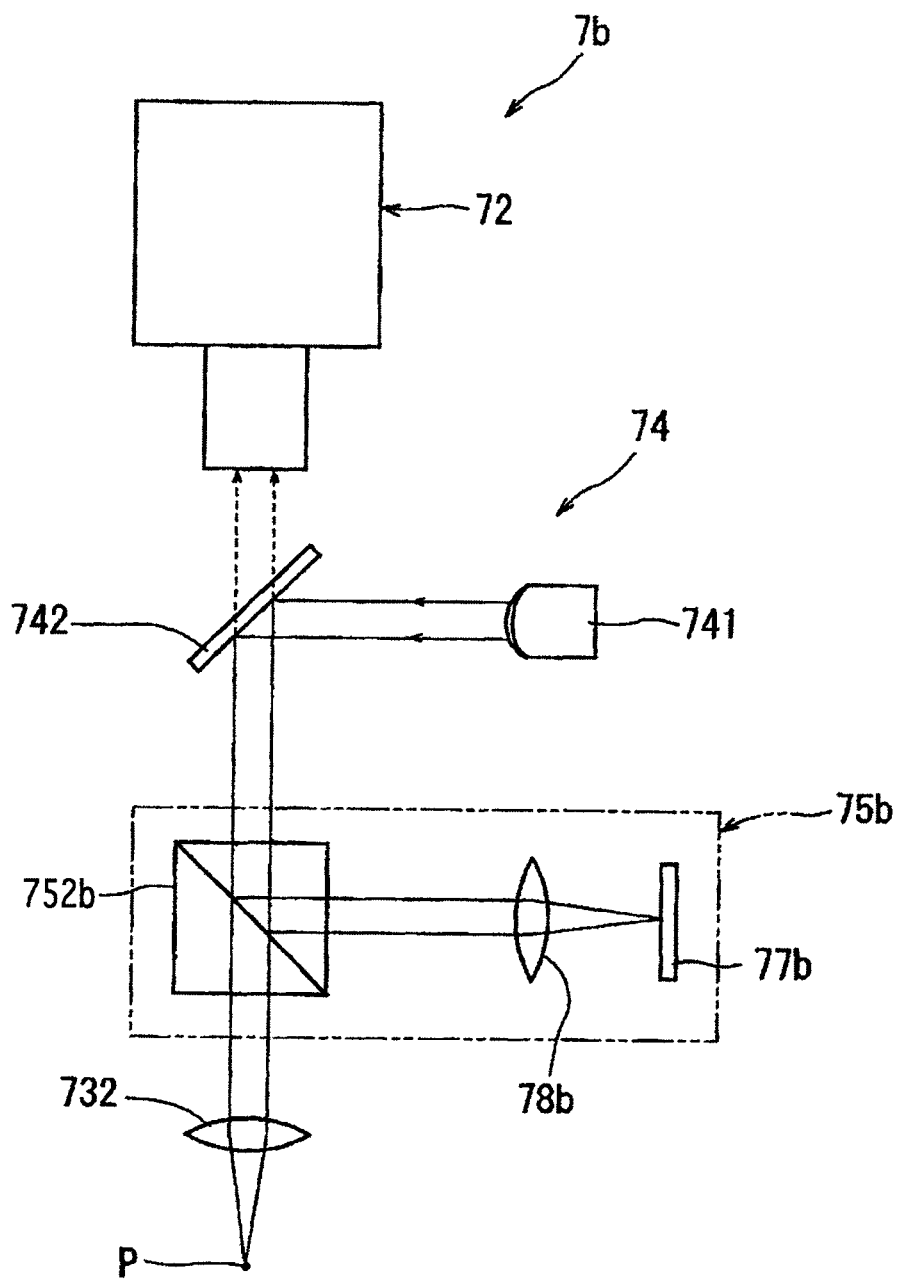
FIG. 11 is a schematic view showing a further preferred embodiment of the three-dimensional imaging mechanism.

A further preferred embodiment of the three-dimensional imaging mechanism in the present invention will now be described with reference to FIG. 11. FIG. 11 shows a three-dimensional imaging mechanism 7b, which is a so-called Linnik type three-dimensional imaging mechanism. The three-dimensional imaging mechanism 7b shown in FIG. 11 is different in the configuration of the interference light generating means from the three-dimensional imaging mechanism 7 shown in FIGS. 3 and 4 and the three-dimensional imaging mechanism 7a shown in FIG. 10.

However, the other components are substantially similar to those shown in FIGS. 3 and 4 and FIG. 10, so that substantially the same parts are denoted by the same reference symbols and the description thereof will be omitted herein.

As shown in FIG. 11, the three-dimensional imaging mechanism 7b includes interference light generating means 75b composed of a first beam splitter 752b, a focusing lens 78b, and a reflection mirror 77b. The first beam splitter 752b is interposed between the second beam splitter 742 of the light applying means 74 and the objective lens 732. The objective lens 732 in this preferred embodiment functions to focus the light transmitted through the first beam splitter 752b. The focusing lens 78b functions to focus the light reflected by the first beam splitter 752b. The reflection mirror 77b is located at a focal position of the light focused by the focusing lens 78b. The light emitted from the light source 741 of the light applying means 74 is reflected by the second beam splitter 742. The light reflected by the second beam splitter 742 is partially transmitted through the first beam splitter 752b, next focused by the objective lens 732, and next reflected at the focal point P on the workpiece. On the other hand, the light reflected by the second beam splitter 742 is partially reflected by the first beam splitter 752b, next focused by the focusing lens 78b, and next reflected on the reflection mirror 77b. The return light from the focal point P interferes with the reflected light from the reflection mirror 77b on the first beam splitter 752b. As a result, interference light having a high intensity is generated and guided toward the imaging device means 72.

While a specific preferred embodiment of the present invention has been described, it should be noted that the present invention is not limited to the above preferred embodiment, but various modifications may be made within the scope of the present invention. For example, while the present invention is applied to a laser processing apparatus in the above preferred embodiment, the present invention may be applied to a cutting apparatus to verify the depth or sectional shape of a cut groove or may be applied to a grinding apparatus to verify the irregular condition of a grinding mark.

Further, in the above preferred embodiment, the three-dimensional image of the laser processed groove 110 is output to the output means 90, and the operator verifies the processed condition of the laser processed groove 110 according to the output from the output means 90. Then, the operator sets proper processing conditions after the verification. As a modification, the laser processing apparatus itself may set proper processing conditions according to the three-dimensional image of the laser processed groove 110. More specifically, the three-dimensional image of a plurality of laser processed grooves formed under proper processing conditions may be preliminarily stored in the random access memory (RAM) 93, and the operator may input the three-dimensional image of laser processed grooves to be formed on a workpiece. Thereafter, the operator may perform test processing to form laser processed grooves on the workpiece under different processing conditions. When the three-dimensional image of any one of the laser processed grooves formed by the test processing comes into coincidence with the three-dimensional image of any one of the laser processed grooves stored in the random access memory (RAM) 93, the processing conditions at this time may be decided as proper processing conditions.

Further, in the case that the pixels arranged at the X and Y coordinates in the imaging device means 72 are 10000× 10000 pixels, a specified part of the pixels, 1000×1000 pixels, for example, may be used. In this case, the memory can be reduced in storage capacity and can also be improved 100 times in storage speed.

The present invention is not limited to the details of the above described preferred embodiment. The scope of the invention is defined by the appended claims and all changes and modifications as fall within the equivalence of the scope of the claims are therefore to be embraced by the invention.

What is claimed is:

1. A processing apparatus comprising:
   workpiece holding means having a holding surface for holding a workpiece;
   processing means, including laser beam applying means, for processing said workpiece held on the holding surface of said workpiece holding means;
   feeding means for relatively moving said workpiece holding means and said processing means in an X direction as a feeding direction;
   an imaging means for detecting a subject area of said workpiece, held on the holding surface of said workpiece holding means, to be laser processed by said laser beam applying means;
   a three-dimensional imaging mechanism for imaging said workpiece held on the holding surface of said workpiece holding means, after laser processing in three dimensions composed of said X direction, a Y direction perpendicular to said X direction, and a Z direction perpendicular to both said X direction and said Y direction and then outputting an image signal obtained above;
   control means for generating a three-dimensional image according to said image signal output from said three-dimensional imaging mechanism; and
   output means for outputting said three-dimensional image generated by said control means,
   wherein said three-dimensional imaging mechanism includes:
   an imaging device having a plurality of pixels arranged in said X direction and said Y direction,
   focusing means opposed to the holding surface of said workpiece holding means,
   light applying means for applying light through said focusing means to said workpiece held on the holding surface of said workpiece holding means,
   interference light generating means for generating interference light according to return light reflected on said workpiece held on the holding surface of said workpiece holding means,
   first Z direction moving means for moving said three-dimensional imaging mechanism in said Z direction independently of said laser beam applying means,
   second Z direction moving means for moving said focusing means in said Z direction, and
   Z position detecting means for detecting the Z position of said three-dimensional imaging mechanism to be moved by said first Z direction moving means; and
   said control means obtains the X and Y coordinates of said pixels in said imaging device means that have captured the interference light having a high intensity as generated by said interference light generating means at every Z position according to a Z position signal from said Z position detecting means and an image signal from said imaging device and then generates said three-dimensional image according to said X and Y coordinates obtained at every Z position.

2. The processing apparatus according to claim 1, wherein said focusing means includes a unit case and an objective lens provided in said unit case;
  said interference light generating means includes:
    a glass plate provided in said unit case so as to be interposed between said objective lens and the holding surface of said workpiece holding means, said glass plate having a central microscopic mirror to generate said interference light, and
    a first beam splitter provided in said unit case so as to be interposed between said glass plate and the holding surface of said workpiece holding means for partially transmitting the light applied from said light applying means and applying the transmitted light to said workpiece held on the holding surface of said workpiece holding means and for also partially reflecting the light applied from said light applying means and directing the reflected light toward said microscopic mirror of said glass plate; and
  said light applying means includes:
    a light source for emitting light and
    a second beam splitter provided between said imaging device and said focusing means for guiding the light emitted from said light source toward said focusing means and also guiding the light reflected from said workpiece held on the holding surface of said workpiece holding means toward said imaging device means.

3. The processing apparatus according to claim 1, wherein said second Z direction moving means comprises a piezoelectric motor.

4. The processing apparatus according to claim 1, wherein:
  said first Z direction moving means comprises:
    a mechanism housing;
    a support case for supporting said mechanism housing;
    an externally threaded rod that is rotatably supported by the support case;
    an internally threaded block provided on the mechanism housing; and
    a drive source for rotationally driving said externally threaded rod,
    wherein said mechanism housing, said support case, said externally threaded rod, said internally threaded block and said drive source are configured and arranged to move said mechanism housing in the Z direction with respect to said support case when said externally threaded rod is rotated by said drive source;
  said second Z direction moving means comprises:
    a unit case configured and arranged to move in the Z direction relative to said mechanism housing;
    an objective lens provided in said unit case; and
    an actuator for moving said unit case in the Z direction relative to said mechanism housing.

5. A processing apparatus comprising:
  workpiece holding means having a holding surface for holding a workpiece;
  processing means, including laser beam applying means, for processing said workpiece held on the holding surface of said workpiece holding means;
  feeding means for relatively moving said workpiece holding means and said processing means in an X direction as a feeding direction;
  a three-dimensional imaging mechanism for imaging said workpiece held on the holding surface of said workpiece holding means in three dimensions composed of said X direction, a Y direction perpendicular to said X direction, and a Z direction perpendicular to both said X direction and said Y direction and then outputting an image signal obtained above;
  control means for generating a three-dimensional image according to said image signal output from said three-dimensional imaging mechanism; and
  output means for outputting said three-dimensional image generated by said control means,
  wherein said three-dimensional imaging mechanism comprises:
    an imaging device having a plurality of pixels arranged in said X direction and said Y direction,
    focusing means opposed to the holding surface of said workpiece holding means,
    light applying means for applying light through said focusing means to said workpiece held on the holding surface of said workpiece holding means,
    interference light generating means for generating interference light according to return light reflected on said workpiece held on the holding surface of said workpiece holding means,
    first Z direction moving means for moving said three-dimensional imaging mechanism in said Z direction independently of said laser beam applying means,
    second Z direction moving means for moving said focusing means in said Z direction, and
    Z position detecting means for detecting the Z position of said three-dimensional moving mechanism to be moved by said first Z direction moving means; and
  wherein said control means obtains the X and Y coordinates of said pixels in said imaging device means that have captured the interference light having a high intensity as generated by said interference light generating means at every Z position according to a Z position signal from said Z position detecting means and an image signal from said imaging device and then generates said three-dimensional image according to said X and Y coordinates obtained at every Z position.

6. The processing apparatus according to claim 5, wherein:
  said first Z direction moving means comprises:
    a mechanism housing;
    a support case for supporting said mechanism housing;
    an externally threaded rod that is rotatably supported by the support case;
    an internally threaded block provided on the mechanism housing; and
    a drive source for rotationally driving said externally threaded rod,
    wherein said mechanism housing, said support case, said externally threaded rod, said internally threaded block and said drive source are configured and arranged to move said mechanism housing in the Z direction with respect to said support case when said externally threaded rod is rotated by said drive source;
  said second Z direction moving means comprises:
  a unit case configured and arranged to move in the Z direction relative to said mechanism housing;
  an objective lens provided in said unit case; and
  an actuator for moving said unit case in the Z direction relative to said mechanism housing.

* * * * *